(12) United States Patent
Admati et al.

(10) Patent No.: US 10,828,429 B2
(45) Date of Patent: Nov. 10, 2020

(54) MICRONEEDLE DEVICE WITH MECHANICAL GUIDE

(71) Applicant: NanoPass Technologies Ltd., Nes Ziona (IL)

(72) Inventors: Gal Admati, Kibbutz Dorot (IL); Yotam Levin, Ness Ziona (IL)

(73) Assignee: NanoPass Technologies Ltd., Ness Ziona (IL)

( * ) Notice: Subject to any disclaimer, the term of this patent is extended or adjusted under 35 U.S.C. 154(b) by 0 days.

(21) Appl. No.: 15/309,803

(22) PCT Filed: Oct. 27, 2016

(86) PCT No.: PCT/IL2016/051162
§ 371 (c)(1),
(2) Date: Nov. 9, 2016

(87) PCT Pub. No.: WO2017/072770
PCT Pub. Date: May 4, 2017

(65) Prior Publication Data
US 2017/0266394 A1     Sep. 21, 2017

Related U.S. Application Data

(60) Provisional application No. 62/246,644, filed on Oct. 27, 2015.

(51) Int. Cl.
| | | |
|---|---|---|
| *A61M 37/00* | (2006.01) | |
| *A61M 5/00* | (2006.01) | |
| *A61M 5/32* | (2006.01) | |
| *A61M 5/42* | (2006.01) | |
| *A61M 5/31* | (2006.01) | |

(52) U.S. Cl.
CPC ............ *A61M 5/425* (2013.01); *A61M 5/002* (2013.01); *A61M 5/3134* (2013.01); *A61M 5/3213* (2013.01); *A61M 5/3275* (2013.01); *A61M 5/3298* (2013.01); *A61M 37/0015* (2013.01); *A61M 2005/3254* (2013.01); *A61M 2037/003* (2013.01); *A61M 2037/0023* (2013.01)

(58) Field of Classification Search
CPC ................ A61M 5/002; A61M 5/3298; A61M 2005/3254; A61M 2037/0023; A61M 2037/003; A61M 1/0039; A61M 1/0086; A61M 5/3134; A61M 5/3213
See application file for complete search history.

(56) References Cited

U.S. PATENT DOCUMENTS

| | | | | |
|---|---|---|---|---|
| 4,836,373 A | * | 6/1989 | Goldman | .............. A61M 5/008 128/919 |
| 5,911,707 A | | 6/1999 | Wolvek | |

(Continued)

FOREIGN PATENT DOCUMENTS

| | | |
|---|---|---|
| WO | 2007066341 | 6/2007 |
| WO | 2013111087 | 1/2013 |

*Primary Examiner* — Tiffany Legette
*Assistant Examiner* — William R Frehe
(74) *Attorney, Agent, or Firm* — Mark M. Friedman

(57) ABSTRACT

A device for delivering a fluid into a biological tissue includes hollow microneedles (10) projecting from a surface (12) of a substrate (14), and a guide element (18) spaced from the substrate. The guide element provides a tissue-contact surface (20) that defines a tissue contact plane oblique to the surface (12) of the substrate (14).

11 Claims, 11 Drawing Sheets

(56) References Cited

U.S. PATENT DOCUMENTS

| | | | |
|---|---|---|---|
| 6,332,875 B2* | 12/2001 | Inkpen | A61M 5/3287 |
| | | | 604/117 |
| 6,743,211 B1* | 6/2004 | Prausnitz | A61B 5/14514 |
| | | | 604/239 |
| 7,648,484 B2 | 1/2010 | Yeshurun et al. | |
| 7,850,657 B2 | 12/2010 | Yeshurun et al. | |
| 7,998,119 B2 | 8/2011 | Yeshurun et al. | |
| 8,007,446 B2 | 8/2011 | Boecker et al. | |
| 2003/0050602 A1* | 3/2003 | Pettis | A61M 5/46 |
| | | | 604/117 |
| 2004/0014790 A1 | 1/2004 | Craig et al. | |
| 2006/0264926 A1 | 11/2006 | Kochamba | |
| 2007/0005017 A1* | 1/2007 | Alchas | A61M 5/425 |
| | | | 604/117 |
| 2007/0118077 A1* | 5/2007 | Clarke | A61M 5/158 |
| | | | 604/117 |
| 2008/0091226 A1 | 4/2008 | Yeshurun et al. | |
| 2009/0012494 A1 | 1/2009 | Yeshurun et al. | |
| 2009/0024795 A1 | 1/2009 | Kobara | |
| 2009/0054842 A1* | 2/2009 | Yeshurun | A61B 5/150099 |
| | | | 604/173 |
| 2010/0137831 A1* | 6/2010 | Tsals | A61M 5/46 |
| | | | 604/506 |
| 2011/0071480 A1* | 3/2011 | Katerkamp | A61B 17/3401 |
| | | | 604/272 |
| 2011/0238038 A1* | 9/2011 | Sefi | A61M 5/46 |
| | | | 604/506 |
| 2012/0022435 A1* | 1/2012 | Ignon | A61B 17/545 |
| | | | 604/22 |
| 2013/0110043 A1 | 5/2013 | Levin | |
| 2014/0148784 A1* | 5/2014 | Anderson | A61M 5/14248 |
| | | | 604/506 |
| 2014/0257190 A1 | 9/2014 | Yue et al. | |
| 2014/0350514 A1 | 11/2014 | Levin | |
| 2015/0038911 A1* | 2/2015 | Levin | A61M 5/347 |
| | | | 604/173 |
| 2015/0051582 A1 | 2/2015 | Pettis et al. | |
| 2015/0258284 A1* | 9/2015 | Fenster | A61M 5/20 |
| | | | 604/111 |
| 2016/0067413 A1* | 3/2016 | Madin | A61M 5/31513 |
| | | | 604/222 |
| 2016/0082239 A1 | 3/2016 | Tamaru et al. | |
| 2016/0184571 A1* | 6/2016 | Admati | A61M 5/31 |
| | | | 604/199 |
| 2016/0235915 A1* | 8/2016 | Cabiri | A61M 5/3202 |

* cited by examiner

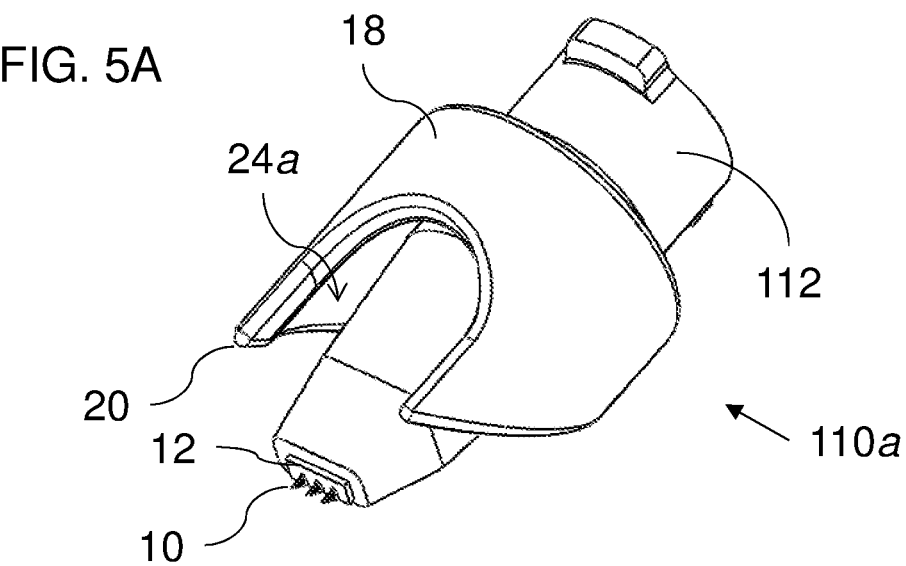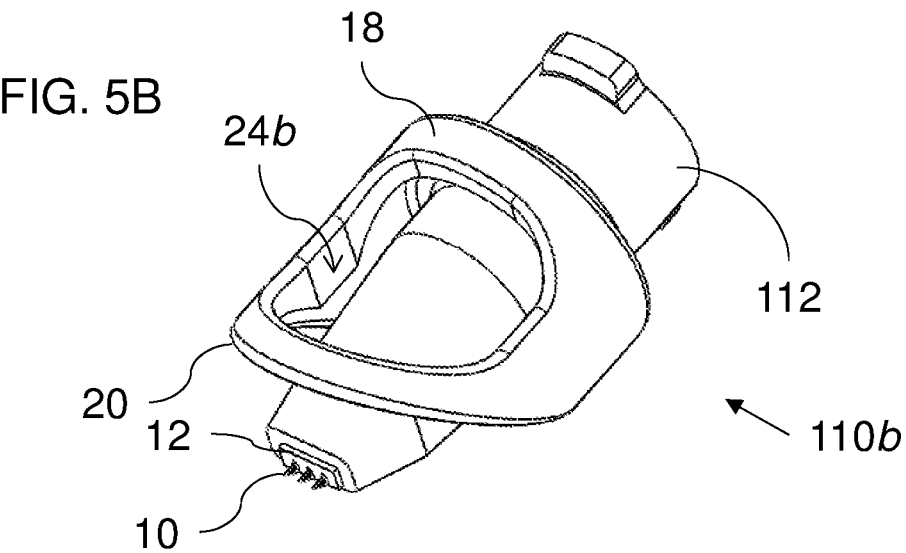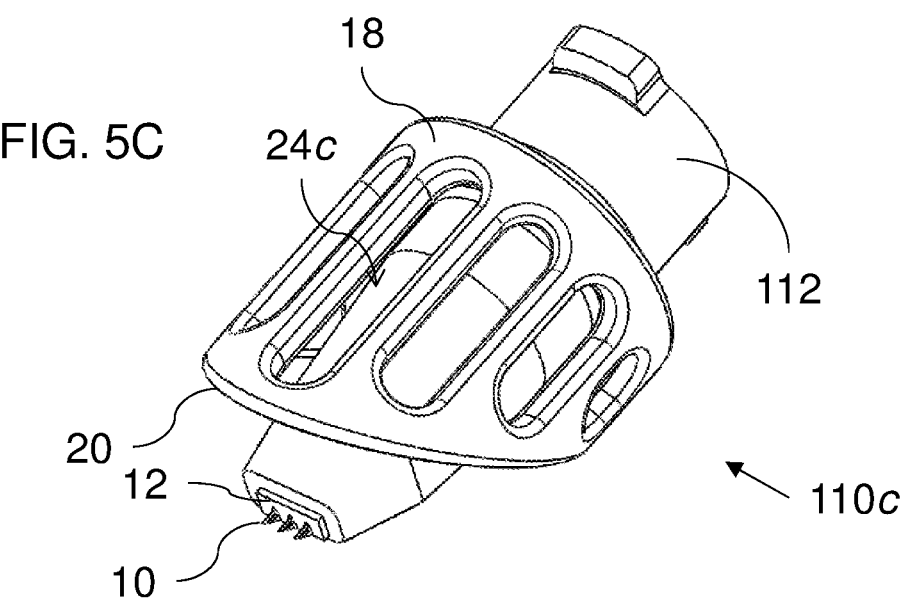

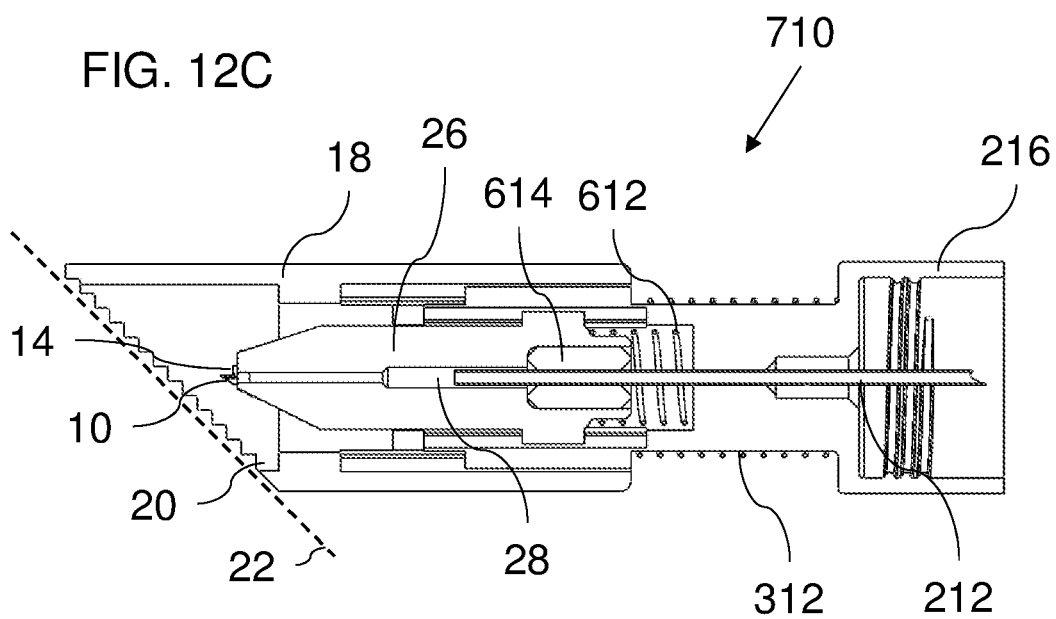
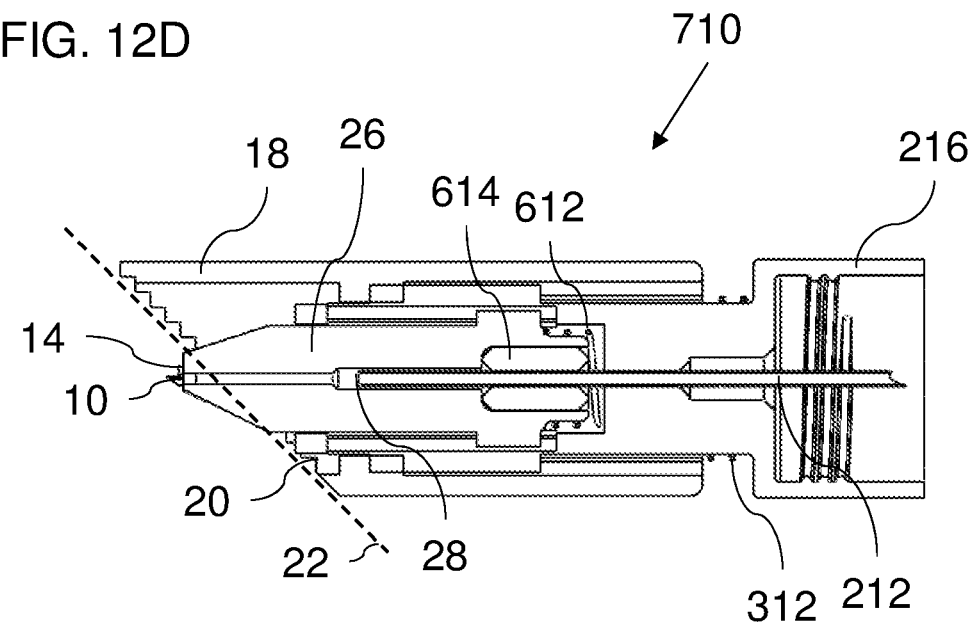

MICRONEEDLE DEVICE WITH MECHANICAL GUIDE

FIELD AND BACKGROUND OF THE INVENTION

The invention relates to devices for delivering a fluid into a biological tissue and, in particular, to a microneedle device with a mechanical guide.

Intradermal injection methods have long been in use for delivery of substances into the skin. Intradermal injection with a standard hypodermic needle requires use of the Mantoux technique, which is known to be difficult and unreliable to perform, and frequently results in leakage or a deeper subcutaneous injection. Without the Mantoux technique, even a 1.5 mm length needle used in a perpendicular injection manner is too long to achieve reliable intradermal injection.

Microneedles are typically relatively short needles with a length generally below 1 mm and a diameter on the micrometer scale, typically a few hundreds of microns at most. Microneedles can be manufactured using various manufacturing techniques ranging from use of steel cannulas, polymers or silicon, and can be made in a variety of production processes including micro-injection molding, hot embossing, wire/laser cutting, radiation and MEMS, among other methods, One particularly advantageous microneedle structure suitable for use in implementing the present invention is described in U.S. Pat. Nos. 7,648,484 and 7,850,657.

Microneedle based injection systems have a number of potential benefits, possibly including one or more of: enhanced effect on immunogenicity, dose sparing (the ability to use a lower amount of antigen for similar or even improved responses), lack of pain or reduced pain, and improved usability. Microneedles offer a relatively simple mechanical technique of direct molecule transfer with the ability to deliver the drug to an exact depth and location in a repetitive and accurate manner, assuming the injection technique is consistent.

A unique approach of non-perpendicular insertion and injection has been disclosed in U.S. Pat. Nos. 7,998,119 and 8,007,446. These designs however may require specific orientation and angle of approach to the skin, which may make repeatability and success rate dependent upon accurate user compliance with the intended mode of use, which may in some cases be somewhat counter-intuitive.

Dosed drug delivery devices and typically Pen Injection Systems (PIS) have long been used for storage and delivery of substances such as insulin, PTH (Para Thyroid Hormone) and other therapeutics, in various sites such as the subcutaneous or intramuscular tissues. The substances are generally delivered using hypodermic needle adapters attached by the end user prior to use, using a threaded female adapter that attaches to a male thread on the PIS for example as defined in ISO 111608-2, 11608-3.

PISs generally include a pen injector with a mechanical system for determining the volume to be injected, a glass replaceable or single use cartridge with the substance and the adapter with needle that is attached prior to injection. The cartridge is generally prefilled with a liquid substance in a clean room aseptic environment. Patent publications WO 2013/111087 and WO 2007/066341 describe various options for providing microneedle adapters for PIS devices.

SUMMARY OF THE INVENTION

The present invention is a microneedle device with a mechanical guide, for delivering a fluid into a biological tissue.

According to the teachings of an embodiment of the present invention there is provided, a device for delivering a fluid into a biological tissue, the device comprising: (a) a hollow microneedle integrally formed with, and projecting from a surface of, a substrate; and (b) a guide element spaced from the substrate, the guide element providing at least one tissue-contact surface defining a tissue contact plane oblique to the surface of the substrate.

According to a further feature of an embodiment of the present invention, the at least one tissue-contact surface substantially circumscribes the substrate.

According to a further feature of an embodiment of the present invention, the hollow microneedle is one of a plurality of hollow microneedles deployed in a linear array of microneedles.

According to a further feature of an embodiment of the present invention, the microneedles project to a microneedle height above the substrate, and wherein the substrate has an edge, the linear array extending parallel to the edge, and located at a distance no more than twice the microneedle height from the edge.

According to a further feature of an embodiment of the present invention, the guide element is deployed with the oblique plane oriented such that, when the tissue-contact surface is brought into contact with the biological tissue, the edge of the substrate is also brought into contact with the biological tissue.

According to a further feature of an embodiment of the present invention, the microneedles are asymmetric microneedles having a tip offset vector defined as a vector from a centroid of a base of each microneedle at the surface of the substrate to a perpendicular projection of a tip of the microneedle onto the surface of the substrate, wherein the microneedles are orientated such that the tip offset vectors are directed away from the edge.

According to a further feature of an embodiment of the present invention, there is also provided aseptic packaging enclosing the guide element and the substrate.

According to a further feature of an embodiment of the present invention, the guide element and the substrate are inseparable components of the device.

According to a further feature of an embodiment of the present invention, the guide element is rigidly mounted in fixed spatial relation to the substrate, the substrate projecting outwards from the tissue contact plane.

According to a further feature of an embodiment of the present invention, the guide element is retractably mounted relative to the substrate, the guide element being resiliently biased to an advanced position in which the substrate lies behind the tissue contact plane, and being retractable to expose the substrate.

According to a further feature of an embodiment of the present invention, there is also provided a supplementary tissue tensioning element coupled to the guide element such that linear retraction of the guide element generates rotation of the tensioning element so as to apply tension to a surface of the biological tissue.

According to a further feature of an embodiment of the present invention, there is also provided a linkage associated with the substrate and the guide element and configured such that linear retraction of the guide element generates a motion of the substrate in a direction with a component perpendicular to the linear retraction.

According to a further feature of an embodiment of the present invention, the substrate is retractably mounted relative to the guide element, the substrate being resiliently biased to an advanced position in which the substrate projects in front of the tissue contact plane.

According to a further feature of an embodiment of the present invention, the device further comprises a female luer connector, the female luer connector being in fluid flow connection for delivering a fluid through the hollow microneedle.

According to a further feature of an embodiment of the present invention, there is also provided a syringe configured to mate with the female luer connector for delivering a fluid via the hollow microneedle.

According to a further feature of an embodiment of the present invention, the device further comprises a septum needle, the septum needle being in fluid flow connection for delivering a fluid through the hollow microneedle.

According to a further feature of an embodiment of the present invention, there is also provided a pen injector having a septum configured to be pierced by the septum needle for delivering a fluid via the hollow microneedle.

BRIEF DESCRIPTION OF THE DRAWINGS

The invention is herein described, by way of example only, with reference to the accompanying drawings, wherein:

FIGS. 5A-5C are isometric views of three variant implementations of the device of FIG. 4A, showing differing implementations of a guide element;

FIGS. 12C and 12D are cross-sectional views taken along a central plane of symmetry of the device of FIG. 12A showing the guide element and the microneedle adapter in non-retracted states and retracted states, respectively.

DESCRIPTION OF THE PREFERRED EMBODIMENTS

The present invention is a microneedle device with a mechanical guide, for delivering a fluid into a biological barrier.

The principles and operation of devices according to the present invention may be better understood with reference to the drawings and the accompanying description.

By way of introduction, microneedle devices of the present invention may be used in a range of different applications. By way of non-limiting examples, the invention will be illustrated with reference to a first set of applications as a syringe adapter for use with a syringe or other fluid delivery system, typically having a leer connector (FIGS. 2 and 4A-6C), and with reference to a second set of applications as an adapter for delivery of fluid from a pen injector device having a septum (FIGS. 3 and 7A-12D). A number of variant embodiments with differing features will be described in the context of each of these applications. It should be noted that, except where clearly stated or self-evident to the contrary, all features described in the context of one application may be used also to advantage, possibly with minor adaptations that will be clear to a person having ordinary skill in the art, in the context of other applications.

Figure 1:
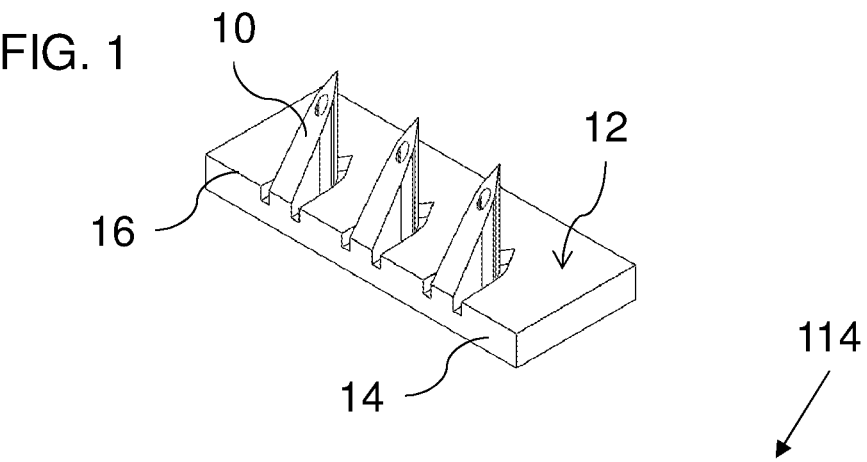
FIG. 1 is an isometric view of a microneedle array for use in devices according to an embodiment of the present invention.
Figure 2:
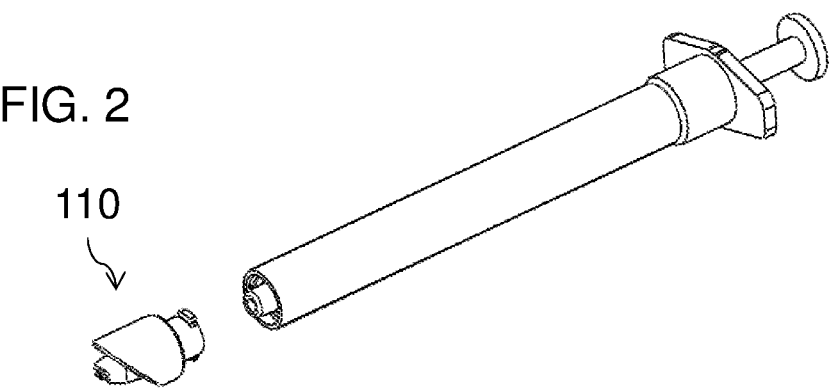
FIG. 2 is an isometric view of a system including a device according to an embodiment of the present invention and a syringe for delivering fluid through the device into a biological barrier.
Figure 3:
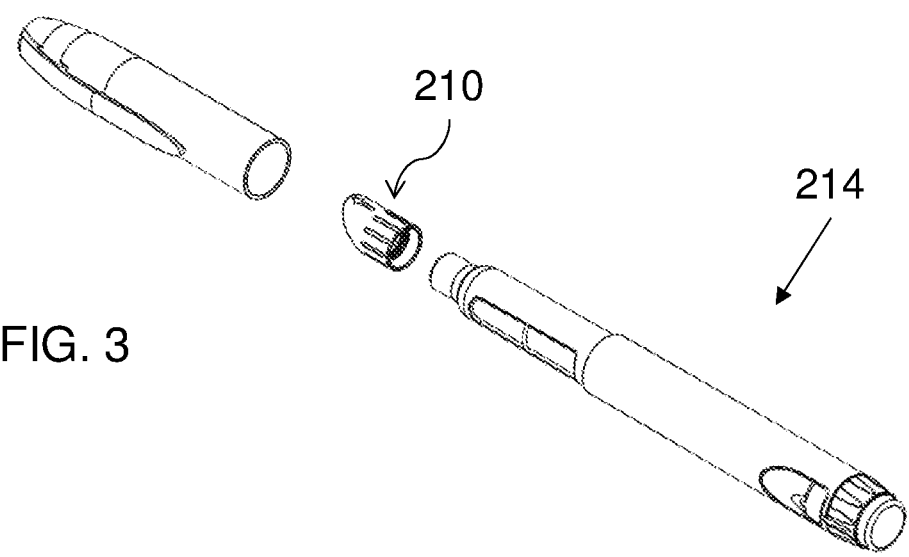
FIG. 3 is an isometric view of a system including a device according to an embodiment of the present invention and a pen injector for delivering fluid through the device into a biological barrier.
Figure 4A:
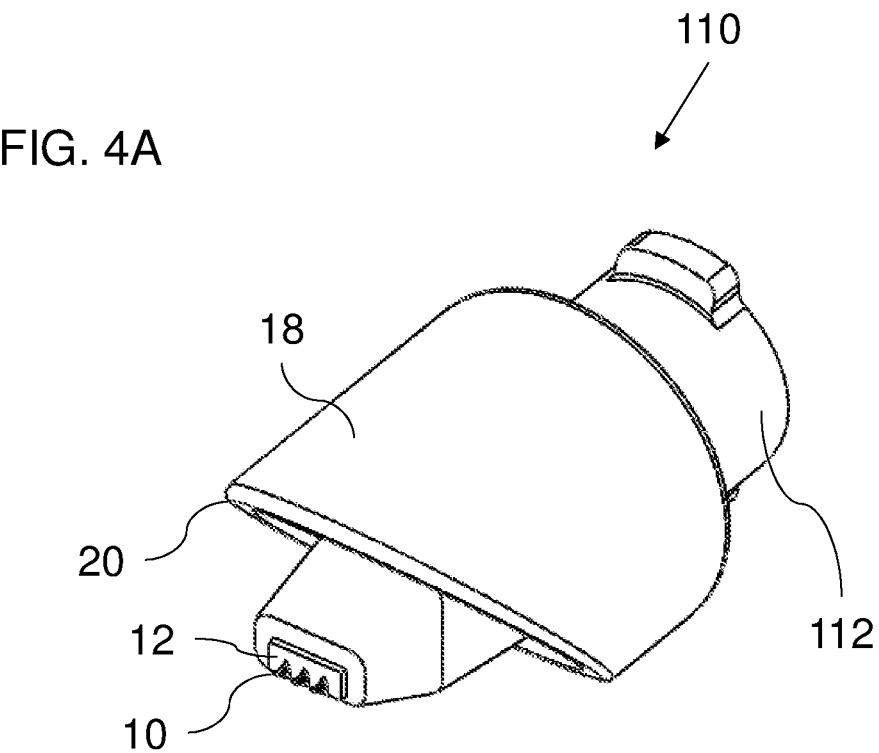
FIG. 4A is an isometric view of the device of FIG. 2.
Figure 4B:
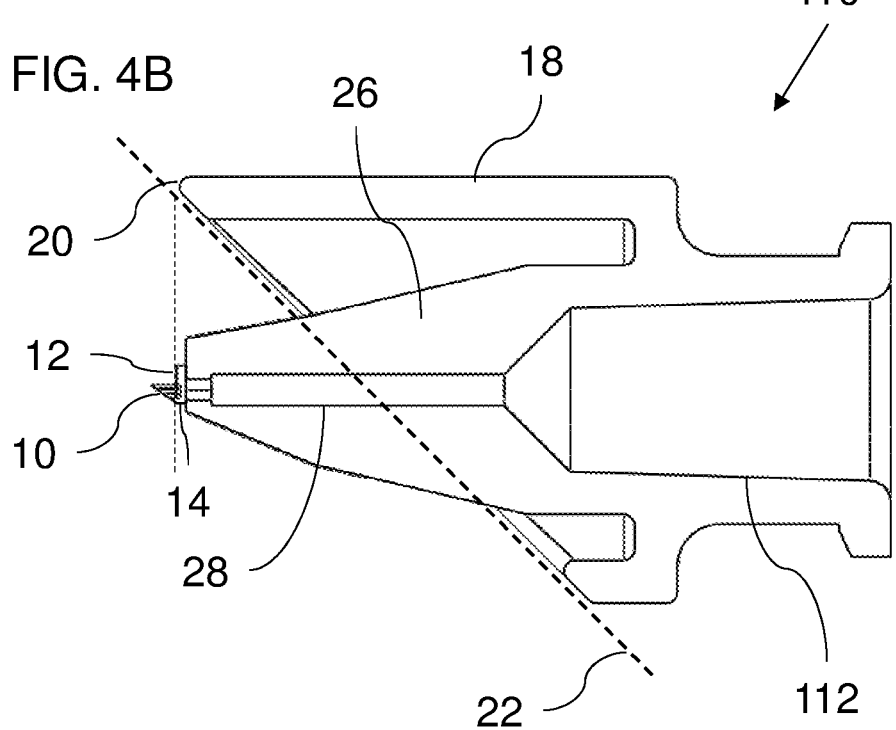
FIG. 4B is a cross-sectional view taken along a central plane symmetry of the device of FIG. 4A.
Figure 6A:
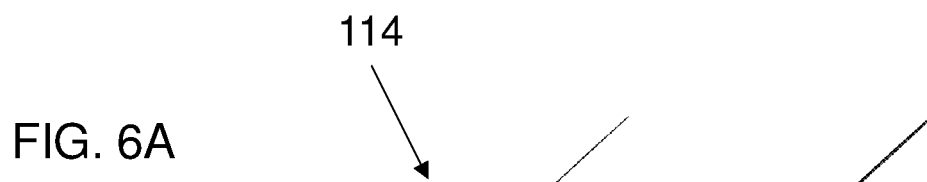
FIG. 6A is an isometric view showing a Luer connector interface for connection of the device of FIG. 2 to the syringe.
Figure 6B:
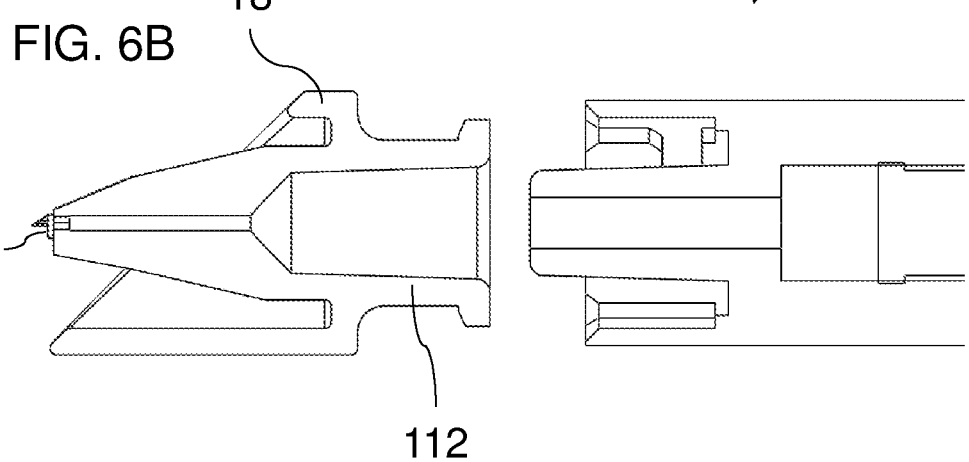
FIGS. 6B and 6C are axial cross-sectional views showing the device of FIG. 2 before and after connection to the syringe.
Figure 6C:
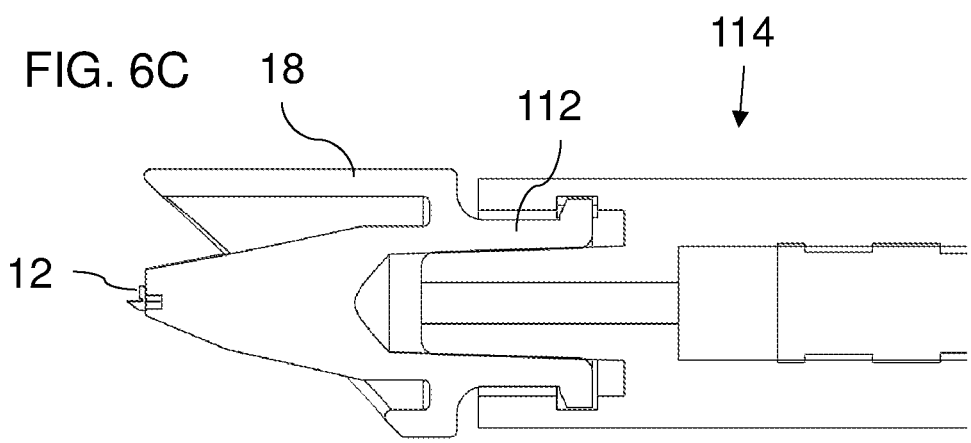

Referring now in generic terms to multiple embodiments of the present invention, and using reference numerals which will be used throughout the description to designate similar features, a device 110, 210, 310, 410, 510, 610, 710 according to certain embodiments of the present invention for delivering a fluid into a biological tissue employs a hollow microneedle 10 integrally formed with, and projecting from a surface 12 of, a substrate 14, as shown in an a magnified view in FIG. 1.

The term "microneedle" is used herein to refer to a projecting feature having a projecting height above surface 12 of no more than about 1 mm, typically between 300 and 1000 microns, and most preferably refers here to microneedles having a height of between about 500 and about 950 microns. In the particularly preferred implementation as illustrated here, hollow microneedle 10 is one of a plurality of hollow microneedles, preferably at least three, deployed as a linear array of microneedles. The linear array of microneedles are preferably arrayed along and adjacent to an edge 16 of substrate 14, edge 16 defining a boundary of surface 12. "Adjacent" in this context preferably refers to proximity of microneedles 10 to edge 16 such that a distance from the base of the microneedles to edge 16 is no more than twice the height to which the microneedles project from surface 12, and more preferably no more than once the height. In the particularly preferred but non-limiting example illustrated here, edge 16 is cut so as to substantially intersect, or even slightly truncate, a sloping surface of the microneedles.

Certain particularly preferred implementations of the present invention employ an asymmetric hollow microneedle structure in which the microneedle tip is offset from the geometric center of the base of the microneedle. In more precise terms, such asymmetric microneedles are referred to as having a "tip offset vector" defined as a vector from a centroid of the geometric outline of the base of the microneedle in a plane corresponding to surface 12 to a perpendicular projection of the tip of the microneedle onto surface 12. A particularly preferred but non-limiting manufacturing technique for hollow microneedles with an asymmetric form as defined here, and corresponding microneedle structures, may be found in the aforementioned in U.S. Pat. Nos. 7,648,484 and 7,850,657. According to such examples, the resulting microneedles are formed by subtractive MEMS techniques from a single crystal wafer of silicon, resulting in projecting microneedles integrally formed with the substrate. As a result of the process, the needles may be surrounded by a channel. In such cases, "surface 12" is taken to be the predominant surface level of the remaining thickness of the substrate disregarding such localized channels or other surface irregularities.

Where asymmetric microneedles with a tip offset vector are used, they are most preferably orientated such that the tip offset vectors are directed away from edge 16. This combination of an array of asymmetric microneedles adjacent to an edge, and with their tip offset vectors directed away from the edge, is uniquely optimized for implementing an angled insertion modality in which the microneedle interface is brought into contact with a biological barrier, such as the skin, with edge 16 pressed against the skin and surface 12 at an oblique angle (typically between about 30 degrees and about 60 degrees) to the undeformed skin surface.

According to certain particularly preferred implementations of the present invention, the device of the present invention further includes a guide element 18, spaced from substrate 14, that provides at least one tissue-contact surface 20 defining a tissue contact plane 22 oblique to surface 12 of the substrate, and preferably at an angle of between about 30 degrees and about 60 degrees thereto. Guide element 18 is preferably deployed with oblique plane 22 oriented such that, when tissue-contact surface 20 is brought into contact with the biological tissue, edge 16 of the substrate is also brought into contact with the biological tissue.

According to the various embodiments of the present invention as described herein, guide element 18 preferably performs one or more of a number of functions. One such function is to provide the user with a visual indication of the orientation at which the device is to be brought into contact with the biological barrier. Specifically, since the tissue-contact surface 20 preferably provides the prevailing visual contour of the device, the user will tend intuitively to orient the device with tissue contact plane 22 generally parallel to the skin surface, thereby ensuring a desired orientation of the device relative to the skin, both in terms of angle relative to the skin surface and in terms of rotation of the delivery device about its own central axis. (In an alternative wording, this orientation may be considered as an orientation on two orthogonal planes relative to the skin, both the angle between the syringe axis and the skin and the angle orthogonal to the first plane between the syringe axis and the skin.) For this purpose, it is typically not critical that the tissue-contact surface 20 actually contact the skin during use, although it clearly may do so. Thus, the tissue-contact surface may be an edge of the guide element, not necessarily deployed to come into contact with the tissue, and the tissue contact plane may in fact be a tissue "guide" plane, visually indicative of a plane parallel to the tissue surface to guide orientation of the device, but not necessarily coming into contact with the tissue. Most preferably, the at least one tissue-contact surface 20 substantially circumscribes substrate 14, meaning that it extends around at least about 210 degrees, and more preferably at least about 270 degrees, around substrate 14. In many particularly preferred cases, tissue-contact surface 20 completely circumscribes substrate 14. Tissue-contact surface 20 may be a continuous surface extending around (substantially circumscribing) substrate 14, or it may be subdivided into two or more separate sections which may have spaces between them.

The devices of the present invention are particularly effective for performing reliable and repeatable intradermal delivery of fluids. Depending on the rate of delivery, effective intradermal delivery typically results in formation of a visible "bleb" which can be viewed as confirmation of successful delivery to the desired intradermal target location. In order to avoid interfering with formation of such a bleb, tissue-contact surface 20 is preferably spaced away from substrate 14, particularly in the distal direction, i.e., in the region adjacent to the skin beyond the microneedles, by a spacing of at least about 3 mm, and more preferably at least about 5 mm.

In order to facilitate visual monitoring of the drug delivery site, penetration of the microneedles and/or formation of a bleb, guide element 18 may advantageously be made from transparent material. Additionally, or alternatively, various implementations of the device of the present invention provide various openings in guide element 18. A number of such examples are illustrated in FIGS. 5A-5C. Specifically, FIG. 5A shows a device 110a in which the most distal region of guide element 18 is formed with an opening 24a which interrupts continuity of tissue-contact surface 20 so that it encompasses more than 270 degrees around substrate 14. FIG. 5B shows a device 110b in which an opening 24b forms an enclosed window in the upward-facing portion of guide element 18, without interrupting continuity of tissue-contact surface 20 around substrate 14. In device 110c (FIG. 5C), a plurality of smaller openings/windows 24c are deployed around guide element 18.

In the examples of device 110, 110a, 110b and 110c, guide element 18 is rigidly mounted in fixed spatial relation to substrate 14 such that no relative motion occurs between skin-contact surface 20 and microneedles 10 during normal use. In order to ensure that the microneedles can be brought effectively into engagement with the skin, substrate 14 may project outwards beyond tissue contact plane 22, as seen clearly in FIGS. 4A-6C. The projection may be between 1 mm and 6 mm, and in certain cases, about 3 min may be preferred, as measured perpendicular to tissue contact plane 22. In alternative implementations, substrate 14 may be deployed substantially on the tissue contact plane 22 or even recessed by up to about 1 mm behind the plane. In this case, the microneedles still penetrate the biological harrier when guide element is pressed against the barrier due to flexibility and resilience of the biological barrier that causes it to bulge slightly within the area pressed-upon by the tissue-contact surface 20. The presence of a tissue contact surface at least partially circumscribing the substrate also serves to limit the depth to which the microneedles can be made to sink into the tissue in the event of application of excess pressure by the user, since the excess pressure is distributed across a relatively large area of the tissue through contact of surface 20.

In order to complete the structure of a device for delivering liquid into a biological barrier, hollow microneedles 10 are in fluid flow connection with a flow path which connects to a source of the fluid to be delivered. Structurally, this is advantageously achieved by attachment of substrate 14, such as by adhesive, to an adapter structure 26 which is formed with at least one internal flow channel 28 which supplies fluid to through-bores at the rear of the substrate which pass through the hollow microneedles. The adapter structure is typically a solid block of material which may be formed from any suitable material, and is typically formed from a molded polymer material. Where a multiple needle microneedle substrate is used, a recess extending behind the microneedles preferably serves as a manifold for delivering the fluid to the bores of all of the needles. Further structural details of the adapter structure, and particularly the "rear" end of the adapter, will depend upon the particular intended application, as will be discussed below.

In the particular examples of FIGS. 2 and 4A-6C, the devices are configured for use with a syringe or other fluid delivery device. One particularly convenient and widely-used connection standard as illustrated here is a Luer or Luer-lock connector 112, allowing use of the device with a wide range of standard syringes 114 (FIG. 2) and connectors of other fluid delivery devices (not shown).

Device 110, and the other embodiments of the devices of the present invention, are preferably implemented as part of a subassembly which further includes a protective cover (not shown) for mechanically protecting the microneedles prior to use, and is typically provided as a sterile subassembly packaged in a blister-pack or other packaging for maintaining sterility, as is known in the art. The device may be manufactured color coded as per the height, diameter or number of microneedles in the microneedle array, in a manner analogous to the color coding system of hypodermic needles that define needle gauge.

Figure 7A:
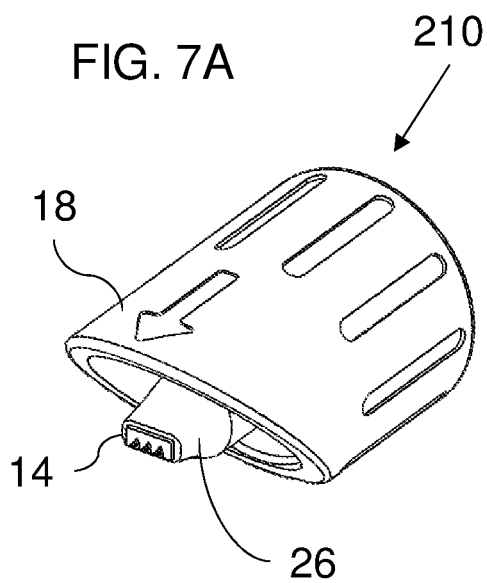
FIGS. 7A and 7B are front and rear isometric views, respectively, of the device of FIG. 3.
Figure 7B:
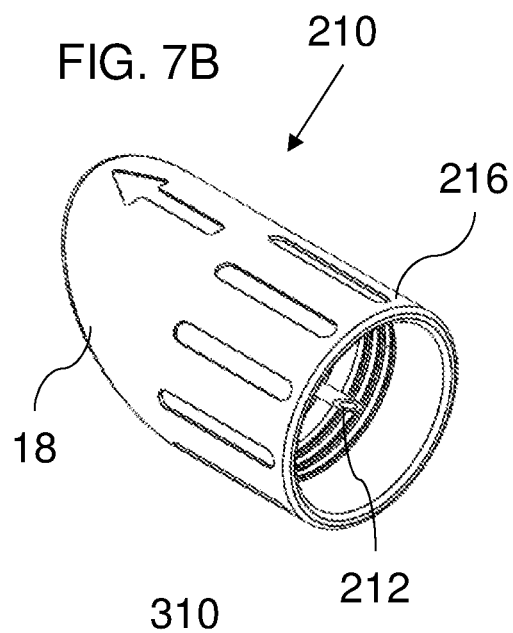

Turning now to FIGS. 3 and 7A-12D, there are shown a further set of implementations of the present invention in which adapter 26 includes a septum needle 212 in fluid flow connection with internal fluid flow channel 28, making the device suited for use with a device such as a pen injector 214 (FIG. 3) having a septum configured to be pierced by the septum needle for delivering a fluid via the hollow microneedle. The pen injector may be any type of pen injector, and is typically an otherwise conventional pen injector such as is commercially available from a range of manufacturers. According to a first subset of these implementations, a rigidly mounted guide element 18 similar to that of any of FIGS. 4A-5C may be integrated with a back-end septum needle 212 as illustrated in FIGS. 7A and 7B. Septum needle 212 can be integrated during a molding process so as to be in sealed interconnection with internal channel 28, and to be surrounded by a suitable attachment configuration, such as a threaded collar 216.

The remaining implementations of FIGS. 8A-12D illustrate further exemplary embodiments of the present invention in which mechanisms are provided for defining various types of relative motion between the microneedle adapter and the guide element and/or one or more additional features of the device in order to provide certain additional functionality and properties. These embodiments are illustrated in a non-limiting manner in relation to a pen-injector adapter, but the corresponding features may also be implemented to advantage in the context of a syringe adapter or other fluid delivery device, with minor modifications as will be clear to a person having ordinary skill in the art.

Figure 8A:
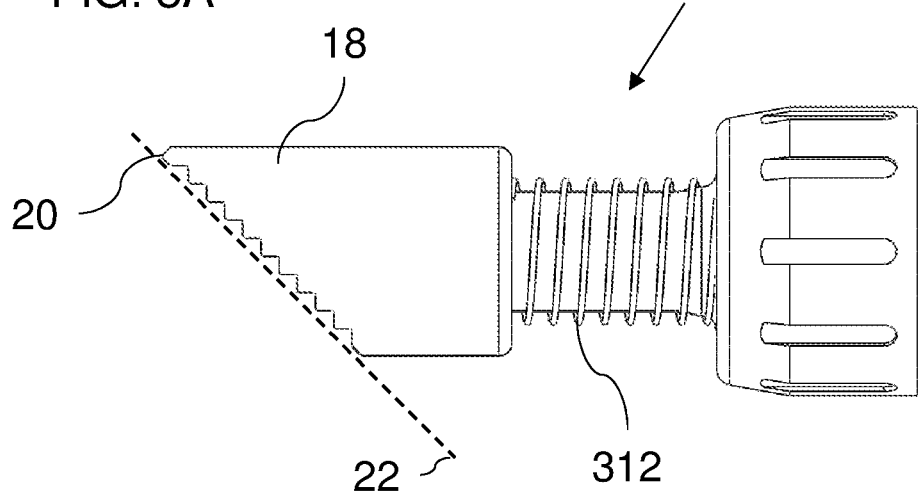
FIG. 8A is a side view of a further embodiment of a device of the present invention having a retractable guide element.
Figure 8B:
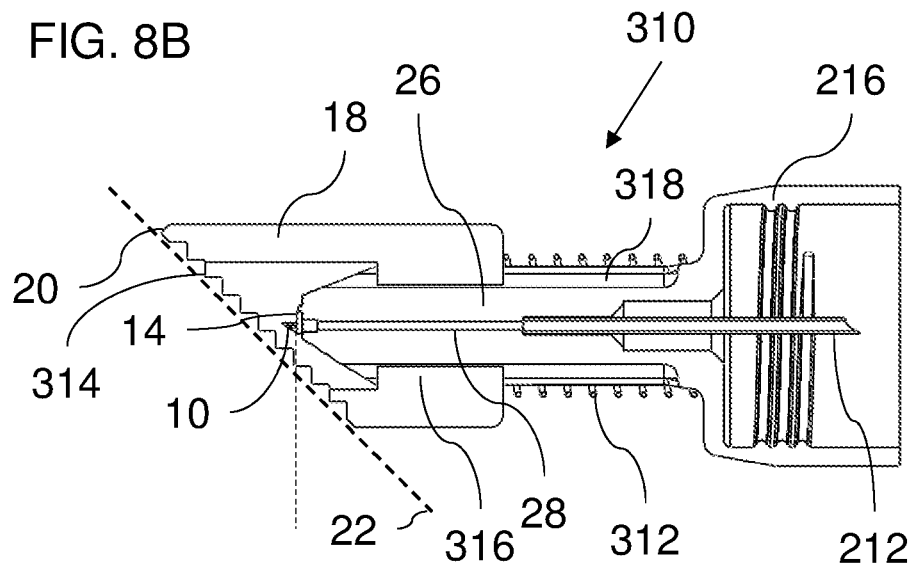
FIG. 8B is a cross-sectional view taken along a central plane of symmetry of the device of FIG. 8A.
Figure 8C:
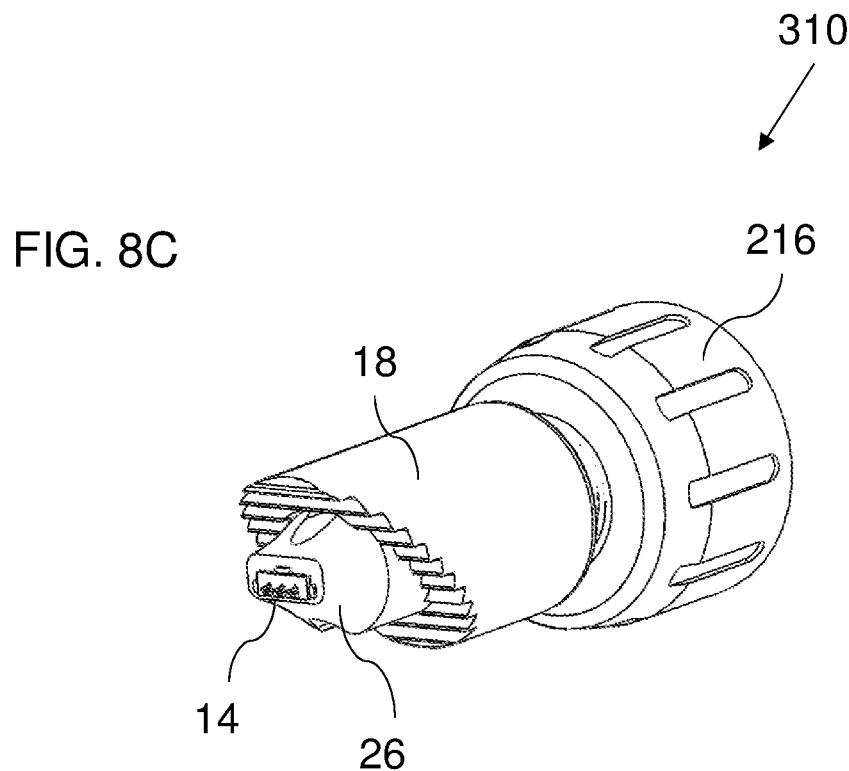
FIG. 8C is a front isometric view device of FIG. 8A with the guide element retracted.
Figure 8D:
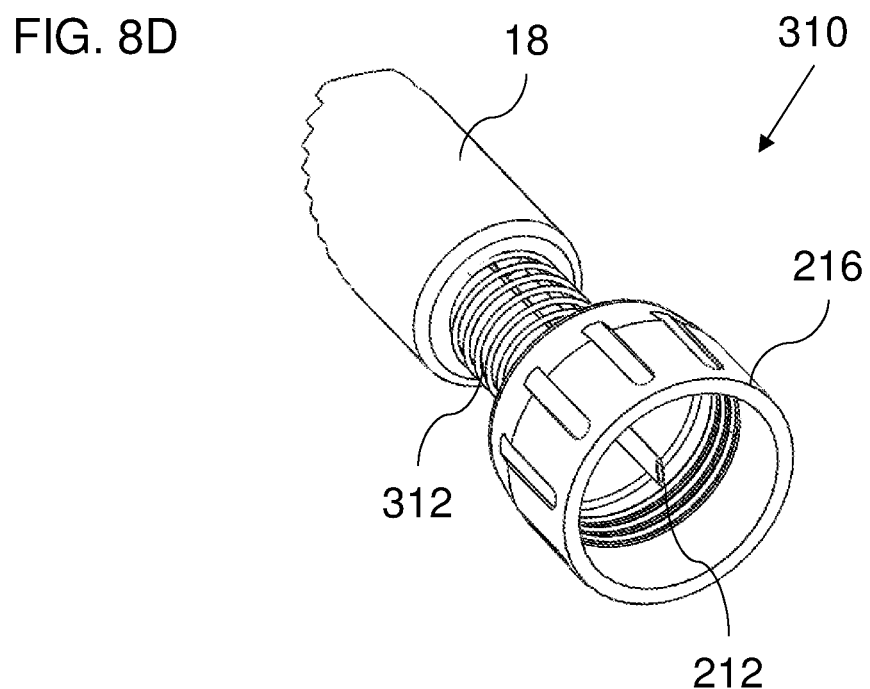
FIG. 8D is a rear isometric view of the device of FIG. 8A.

Turning now to FIGS. 8A-8D, these illustrate a device 310 which is structurally and functionally similar to device 210 of FIG. 7, with equivalent features labeled similarly. In this embodiment, guide element 18 is retractably mounted relative to substrate 14, i.e., so that it can slide rearwardly relative to the microneedles between an initial forward position, as shown in FIGS. 8A and 8B, and a retracted position as shown in FIG. 8C. Guide element 18 is resiliently biased to the advanced (forward) position by a suitable biasing element, such as spring 312. In the forward position, substrate 14 lies behind tissue contact plane 22, thereby providing a degree of protection to the microneedles from accidental damage and/or to the user from needle pricks prior to use. In use, tissue-contact surface 20 is brought into contact with the tissue barrier and gentle forward pressure is applied by the user, causing guide element to retract, exposing substrate 14 so that microneedles 12 penetrate into the tissue. A fully advanced state of the microneedles, corresponding to the fully retracted state of guide element 18, preferably has a geometry functionally equivalent to the device of FIG. 7A.

In order to ensure linear retractability of guide element 18 while maintaining the required rotational orientation of the guide element relative to the microneedle array, the outer surface of adapter 26 and an inner parts of guide element 18 are preferably configured to provide a linear sliding bearing configuration. In the example illustrated here (see FIG. 8B), inward-projecting ridges 316 engage corresponding slots 318 formed along the body of adapter 26.

The retractable guide element 18 may contribute to effective penetration of the microneedles into the tissue barrier by applying enhanced tension to the tissue surface during insertion. Specifically, where tissue-contact surface 20 comes into contact with the tissue before contact of the microneedles, the contact surface effectively immobilizes a region of tissue. The subsequent motion of the substrate and microneedles at an angle against the tissue surface tends to stretch the tissue surface and enhance penetration of microneedles 10 into the tissue. In order to enhance friction between tissue-contact surface 20 and the tissue, surface 20 may advantageously be formed with a plurality of steps 314 as shown, and/or with other types of projections or other friction-enhancing mechanical features.

Here too, device 310 and the subsequent embodiments of the devices of the present invention are preferably implemented as part of a subassembly which further includes a protective cover (not shown) for mechanically protecting the microneedles prior to use. Despite the required relative motion, the retractable guide element is implemented as an inseparable component interconnected with the microneedle adapter and chip, provided as a sterile subassembly packaged in a blister-pack or other packaging for maintaining sterility. "Inseparable" in this context refers to interconnection such that the parts cannot readily be separated manually in a non-destructive manner.

Figure 9A:
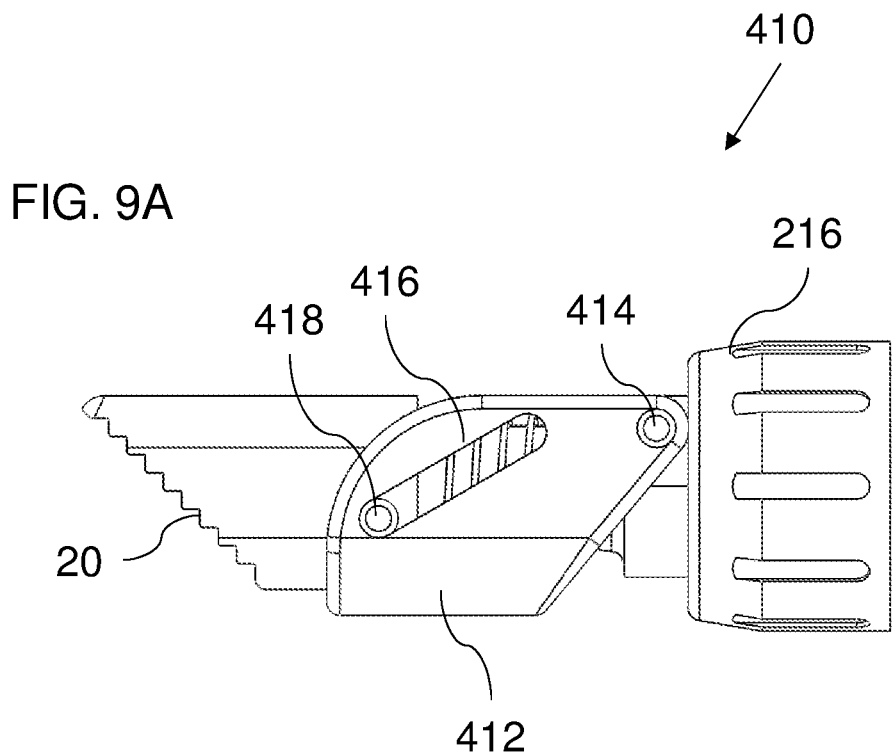
FIG. 9A is a side view of a further embodiment of a device of the present invention having a retractable guide element and a supplementary tissue-tensioning flap.
Figure 9B:
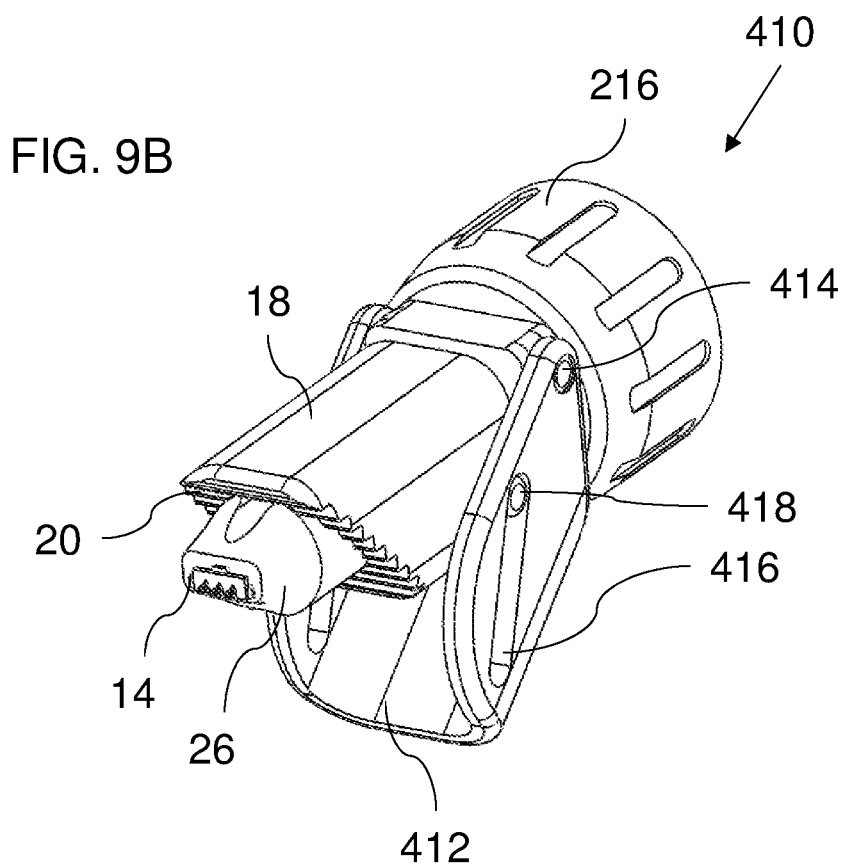
FIG. 9B is a front isometric view of the device of FIG. 9A with the guide element retracted and the supplementary tissue-tensioning flap open.

Turning now to FIGS. 9A and 9B, there is shown a further variant implementation of a device 410, generally similar to device 310, in which a supplementary tissue tensioning element 412 is coupled to guide element 18 so that linear retraction of guide element 18 generates rotation of tensioning element 412, thereby applying tension to a surface of the biological tissue. In the example shown here, supplementary tissue tensioning element 412 is implemented as a flap which is hingedly mounted at a pair of coaxial fixed pins 414 mounted to threaded collar 216, and has bilateral inclined slots 416 which is engaged by a pair of coaxial pins 418 projecting from guide element 18. As a result of this structure, rearward motion of guide element 18 against spring bias (similar to that described above in the context of device 310) displaces pins 418 along inclined slots 416, thereby forcing tissue tensioning element 412 to rotate to that the flap opens rearwardly relative to the direction in which the microneedles are advancing. This coordinated motion applies rearward tensioning to the tissue surface, thereby enhancing penetration of the microneedles. Optionally, a distal edge of tissue tensioning element 412 may be textured or otherwise provided with ridges, teeth or the like (not shown) to increase frictional engagement with the biological barrier and thereby enhance the tensioning effect. In all other respects, device 412 is similar in structure and function to device 312 described above.

Figure 10A:
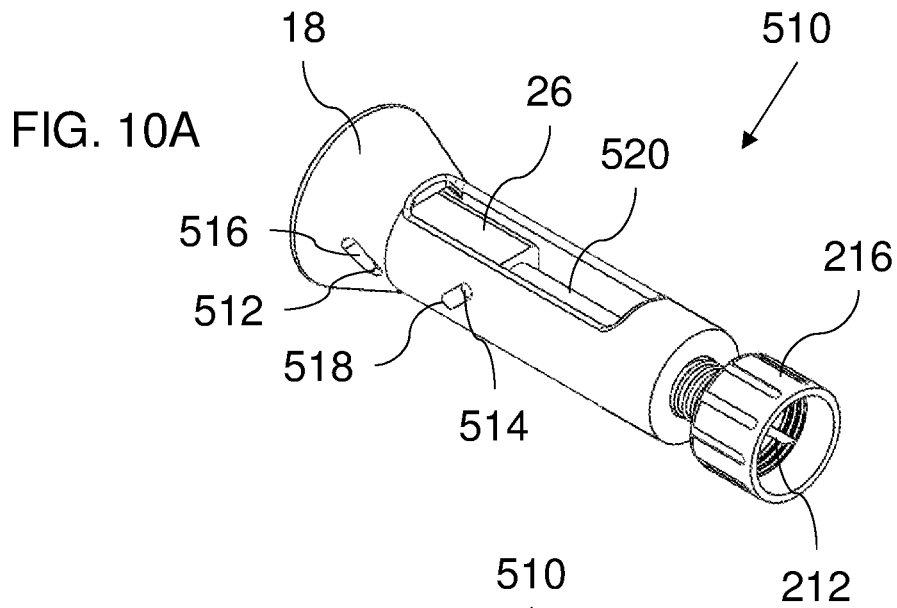
FIG. 10A is an isometric view of a further embodiment of a device of the present invention having a retractable guide element and a linkage for generating transverse motion of the microneedles.
Figure 10B:
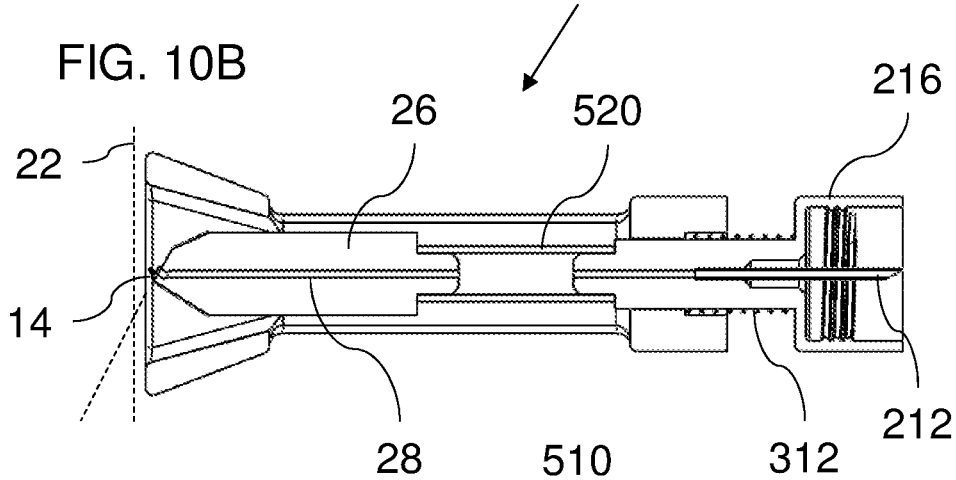
FIGS. 10B and 10C are cross-sectional views taken along a central plane of symmetry of the device of FIG. 10A showing the guide element in a non-retracted state and a retracted state, respectively.
Figure 10C:
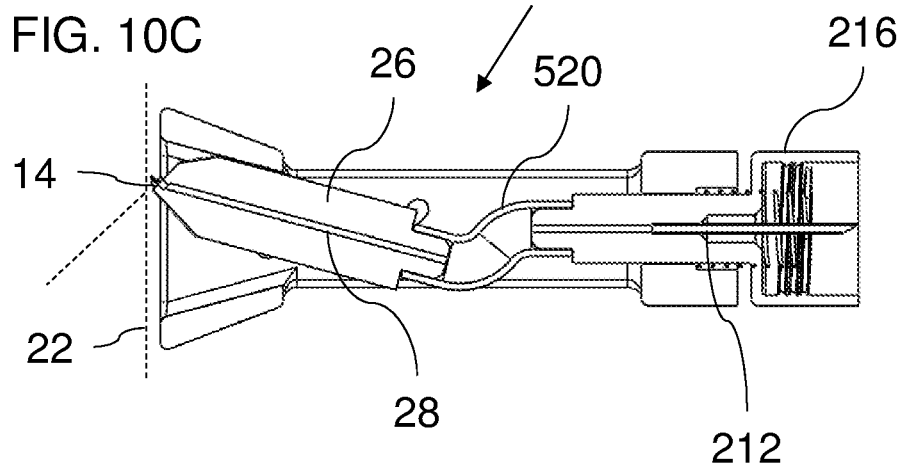

Turning now to FIGS. 10A-10C, there is shown a device 510 according to a further variant implementation of the present invention. Here too, the device is provided with a retractable guide element 18 essentially similar to devices 310 and 410. In this case, a linkage associated with substrate 14 and guide element 18 is configured such that linear retraction of guide element 18 generates a motion of substrate 14 in a direction with a component perpendicular to the linear retraction.

In the particular example illustrated here, adapter 26 is provided with pins 512 and 514 which engage oppositely inclined slots 516 and 518, respectively, formed in an elongated guide element 18. Angular mobility of adapter 26 is facilitated by a flexible fluid connection tube 520 which bridges between internal fluid flow path 28 and the channel associated with septum needle 218. As a result of this structure, on resilient retraction of retractable guide element 18, corresponding to the transition from FIG. 10B to FIG. 10C, motion of pin 514 along slot 518 displaces a rear portion of adapter 26 in a first direction while motion of pin 512 along slot 516 displaces the front portion of adapter 26 in a second direction, opposite to the first direction, thereby generating a rotation of adapter 26. This rotation combined with the retraction of the guide element causes a motion of substrate 14 and microneedles 10 in a direction which has a component perpendicular to the direction of retraction, thereby applying tension to the tissue which is held in place by tissue-contact surface 20 and thus enhancing penetration of the microneedles.

In this exemplary implementation, tissue contact plane 22 is shown as perpendicular to the axis of retraction of guide element 18. The oblique angle between surface 12 and tissue contact plane 22 is here ensured by an inclination of the surface of the adapter 26 to which substrate 14 is applied, as illustrated in FIG. 10B. This oblique angle is further increased during use of the device by the aforementioned rotation of adapter 26. In the non-limiting example illustrated here, the initial oblique angle is roughly 30 degrees, and increases to 50-60 degrees at full retraction of guide element 18.

In all other respects, the structure and operation of device 510 will be understood by reference to the other devices described above.

Figure 11A:
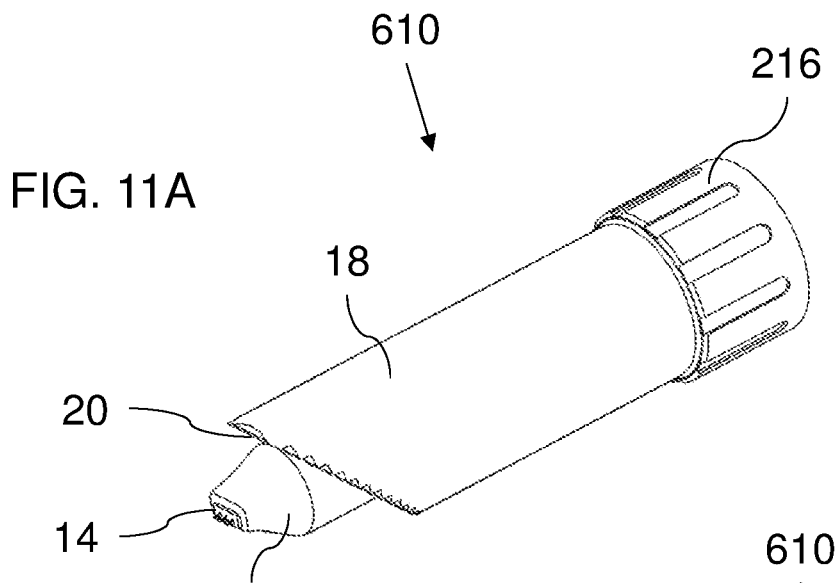
FIG. 11A is an isometric view of a further embodiment of a device of the present invention having a retractable microneedle adapter.
Figure 11B:
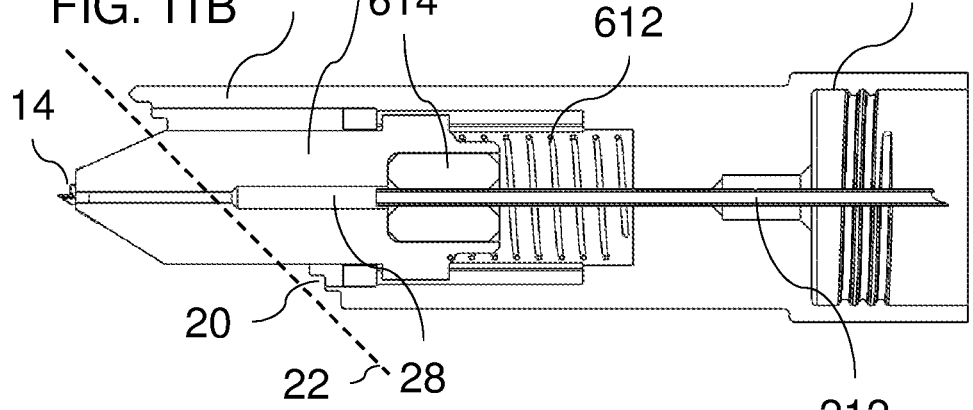
FIGS. 11B and 11C are cross-sectional views taken along a central plane of symmetry of the device of FIG. 11A showing the microneedle adapter in a non-retracted state and a retracted state, respectively.
Figure 11C:
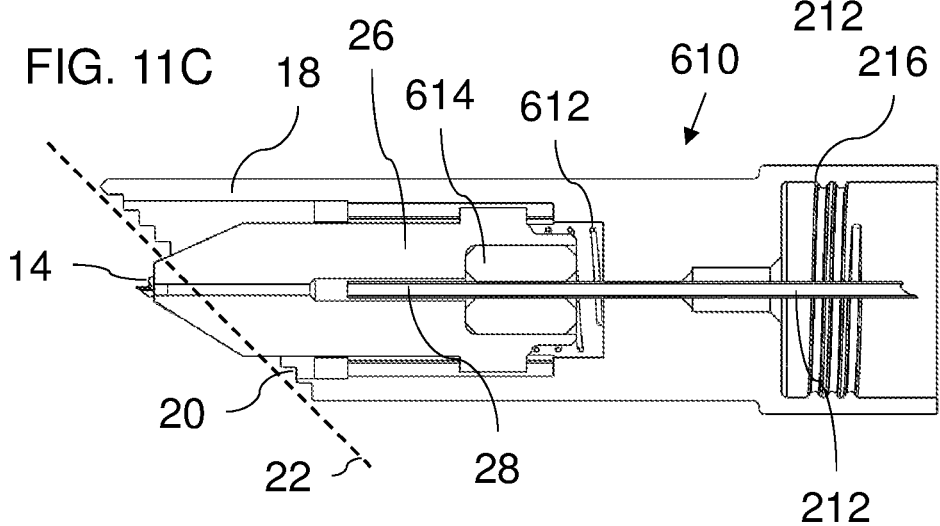
Figure 12A:
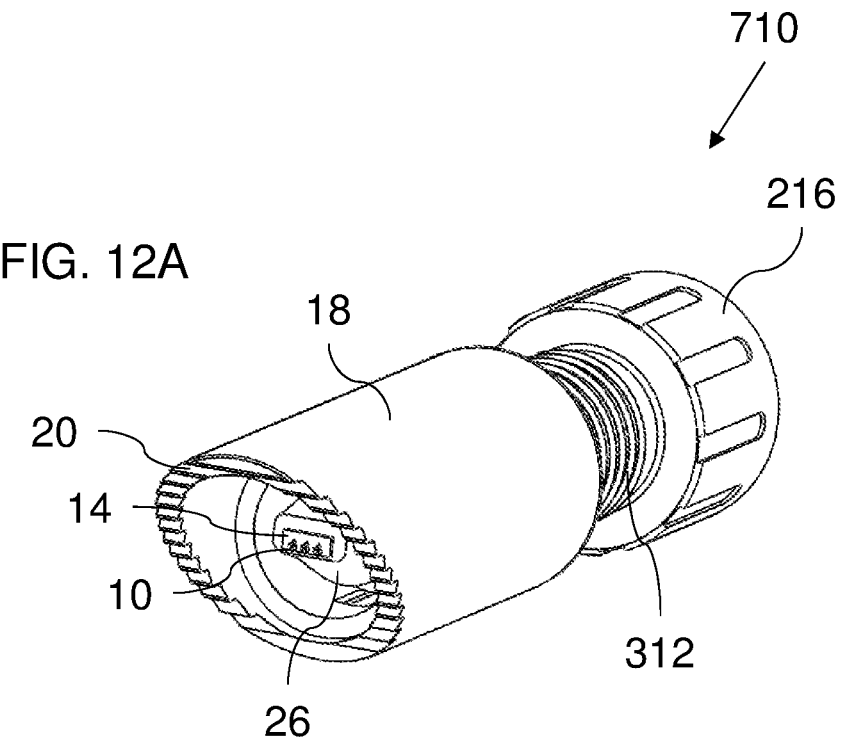
FIGS. 12A and 12B are front and rear isometric views, respectively, of a further embodiment of a device of the present invention having both a retractable guide element and a retractable microneedle adapter.
Figure 12B:
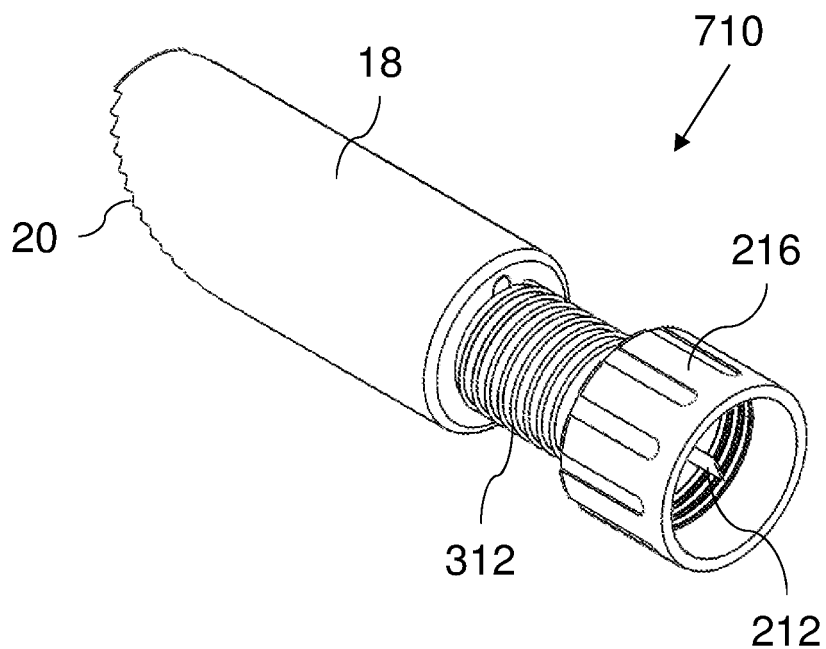

Turning now to FIGS. 11A-11C, there is shown a device 610 according to a further variant implementation of the present invention. In this case, it is substrate 14 and adapter 26 that are retractably mounted relative to guide element 18, while guide element 18 itself is rigidly mounted relative to threaded cap 216. Adapter 26 is resiliently biased to an advanced (forward) position (FIG. 11B), for example, by a spring 612, so that substrate 14 projects in front of tissue contact plane 22. Spring 612 serves to limit the contact force between the microneedles and the biological barrier as increased force applied by the user results in retraction of the microneedles rather than excess contact force. A fully retracted position (e.g., FIG. 11C) may correspond to a position in which the microneedles still project somewhat beyond tissue contact plane 22, or where the microneedles are flush with, or recessed behind, contact plane 22. At some point in the retraction, tissue contact surface 20 comes into contact with the tissue surface, and further force applied by the user tends to be distributed via guide element 18, thereby continuing to limit the contact force of the microneedles against the biological barrier to a desired range of contact force.

Sealed flow interconnection between internal flow channel 28 and septum needle 212 is preferably maintained during motion of adapter 26 by a sliding seal 614 which slides along an extended shaft of septum needle 212. The seal may be made of PTFE, silicone or any other material that can maintain a sliding seal along a cannula Turning finally to FIGS. 12A-12D, there is shown a device 710 according to a further variant implementation of the present invention. Device 710 may be regarded as a combination of the features of devices 310 and 610 in that it combines the retractable guide element 18 of device 310 together with the retractable adapter 26 of device 610. All components are numbered according to the corresponding features of the above embodiments, and will be understood by reference to the corresponding description above. This implementation combines the advantages of protection of the microneedles prior to use and tensioning of the biological barrier provided by resiliently retractable guide element 18 together with the contact force limiting functionality of the retractable adapter. Specifically, during use, tissue-contact surface 20 first comes into contact with the tissue, defining the orientation of the device relative to the tissue surface and gripping the underlying region of skin. As contact pressure is increased, spring 312 is compressed and guide element 18 retracts until microneedles 10 come into contact with the tissue. Additional contact pressure applied beyond that point then starts to compress spring 612, thereby limiting the pressure which is applied to microneedles 10 against the tissue so that it remains within a desired range of values.

It should be noted that all of the various retracting and tensioning features described above with reference to FIGS. 8A-12D may be implemented with alternative back-end interfaces, such as a Luer connector or other standard or proprietary interface, for use with a syringe, for connection directly or via tubing to a pump, or with any other desired fluid delivery device.

The term "biological barrier" or "tissue" as used herein refers to any tissue surface into which fluid is to be introduced, including but not limited to, intradermal delivery into the skin, intra-ocular delivery into or through selected layers of the conjunctiva, sclera, and/or choroid or other ocular tissue, and into the surface of any other body membrane or organ, whether normally exposed or temporarily rendered accessible during a surgical procedure.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

What is claimed is:

1. A device for delivering a fluid into a biological tissue, the device comprising:
   (a) a linear array of a plurality of hollow microneedles integrally formed with, and projecting from a surface of, a substrate; and
   (b) a guide element spaced from said substrate, said guide element providing at least one tissue-contact surface substantially circumscribing said substrate and defining a tissue contact plane oblique to said surface of said substrate, said at least one tissue-contact surface being spaced away from said substrate so as to avoid said at least one tissue-contact surface applying pressure to the biological tissue in a region of formation of an intradermal bleb distal to said plurality of hollow microneedles when a fluid is delivered into the biological tissue via said plurality of hollow microneedles, wherein said guide element is rigidly mounted in fixed spatial relation to said substrate, said substrate projecting outwards from said tissue contact plane.

2. The device of claim 1, wherein said plurality of hollow microneedles project to a microneedle height above said substrate, and wherein said substrate has an edge, said linear array extending parallel to said edge, and located at a distance no more than twice said microneedle height from said edge.

3. The device of claim 2, wherein said guide element is deployed with said oblique tissue contact plane oriented such that, when said at least one tissue-contact surface is brought into contact with the biological tissue, said edge of said substrate is also brought into contact with the biological tissue.

4. The device of claim 2, wherein said plurality of hollow microneedles are asymmetric microneedles having a tip offset vector defined as a vector from a centroid of a base of each microneedle at the surface of said substrate to a perpendicular projection of a tip of said each microneedle onto the surface of said substrate, wherein said each microneedle is oriented such that said tip offset vector is directed away from said edge.

5. The device of claim 1, further comprising aseptic packaging enclosing said guide element and said substrate.

6. The device of claim 1, wherein said guide element and said substrate are inseparable components of the device.

7. The device of claim 1, wherein the device further comprises a female luer connector, said female luer connector being in fluid flow connection for delivering the fluid through said plurality of hollow microneedles.

8. The device of claim 7, further comprising a syringe configured to mate with said female luer connector for delivering the fluid via said plurality of hollow microneedles.

9. The device of claim 1, wherein the device further comprises a septum needle, said septum needle being in fluid flow connection for delivering the fluid through said plurality of hollow microneedles.

10. The device of claim 1, wherein said guide element is formed with at least one opening deployed to allow visual monitoring of the plurality of hollow microneedles.

11. The device of claim 1, wherein said at least one tissue-contact surface is spaced away from said substrate by at least 5 millimeters.

* * * * *